United States Patent [19]

Bjerknes

[11] Patent Number: 5,358,406
[45] Date of Patent: Oct. 25, 1994

[54] METHOD FOR ADAPTING AND IMPLANTING A DENTAL PORCELAIN CHIP, AND THE CHIP

[76] Inventor: Bård Bjerknes, Vesterasveien 40B, Oslo, Norway, N-0283

[21] Appl. No.: 66,085
[22] PCT Filed: Nov. 26, 1991
[86] PCT No.: PCT/NO91/00148
§ 371 Date: May 26, 1993
§ 102(e) Date: May 26, 1993
[87] PCT Pub. No.: WO92/09241
PCT Pub. Date: Jun. 11, 1992

[30] Foreign Application Priority Data
Nov. 26, 1990 [NO] Norway ................. 905109

[51] Int. Cl.$^5$ ............... A61C 5/04; A61C 5/00
[52] U.S. Cl. .................. 433/226; 433/215
[58] Field of Search ........... 433/215, 226, 228.1, 433/218, 219

[56] References Cited

U.S. PATENT DOCUMENTS

| | | | |
|---|---|---|---|
| 4,182,312 | 1/1980 | Mushabac | 433/68 |
| 4,575,805 | 3/1986 | Moermann et al. | 364/474 |
| 4,654,007 | 3/1987 | Sigler et al. | 433/226 |
| 4,655,710 | 4/1987 | Andersson et al. | 433/218 X |
| 4,964,770 | 10/1990 | Steinbichler et al. | 433/223 |
| 4,971,558 | 11/1990 | Jacobi | 433/226 |
| 5,106,303 | 4/1992 | Oden et al. | 433/228.1 X |

FOREIGN PATENT DOCUMENTS

0054785 4/1981 European Pat. Off.
0311214 6/1988 European Pat. Off.

Primary Examiner—Gene Mancene
Assistant Examiner—Nicholas D. Lucchesi
Attorney, Agent, or Firm—Brumbaugh, Graves, Donohue & Raymond

[57] ABSTRACT

A method is disclosed for adapting and implanting at least one dental porcelain chip (9) in a cavity (2, 3, 4). The cavity and each porcelain chip (9) are subjected to necessary etching, silanization, and application of a binder before implantation occurs. At first, a moulding (10a) is made of the cavity (2, 3, 4), whereupon the moulding (10a) is fastened to the porcelain chip (9). Then the porcelain chip is contour worked to substantially the same shape as the moulding (10a), and the formed chip (9c) is placed in the cavity and fastened by means of a binder to the original tooth (1).

11 Claims, 2 Drawing Sheets

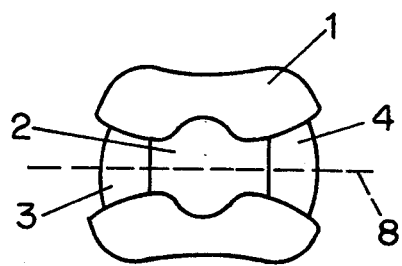
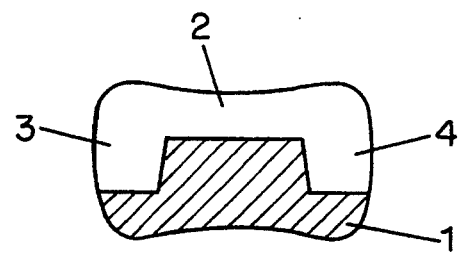
FIG. 1A    FIG. 1B
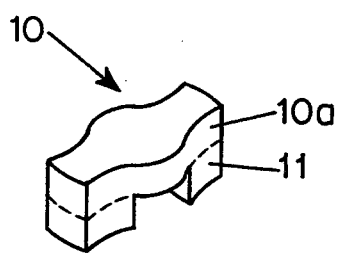
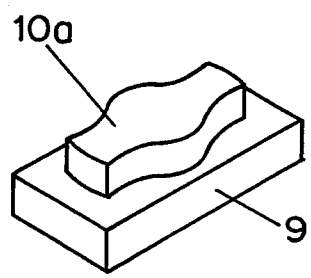
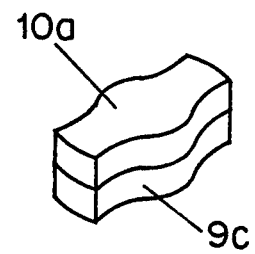
FIG. 2A    FIG. 2B    FIG. 2C
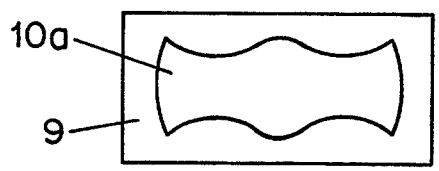
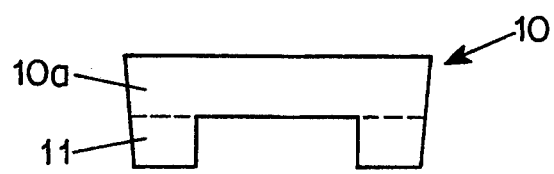
FIG. 2D    FIG. 2E
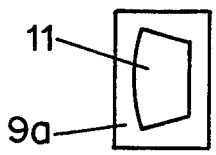
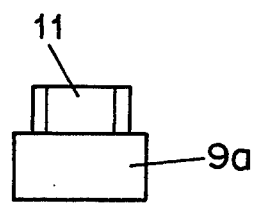
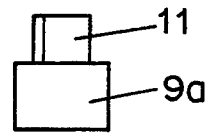
FIG. 3A    FIG. 3B    FIG. 3C
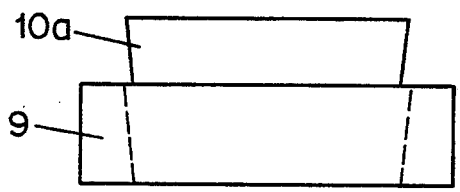
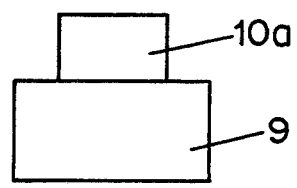
FIG. 4A    FIG. 4B

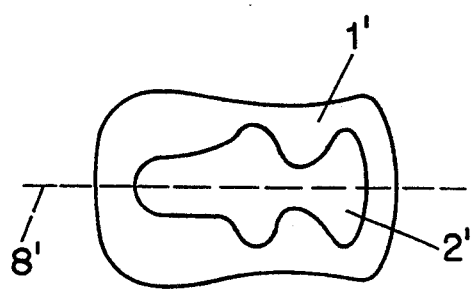
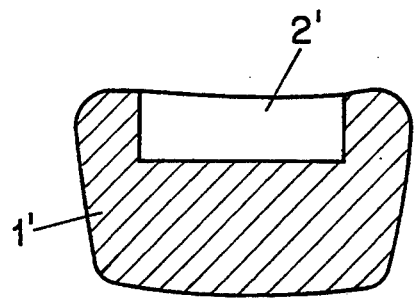
FIG. 5A  FIG. 5B
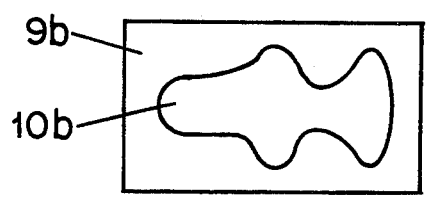
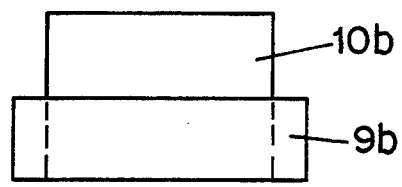
FIG. 6A  FIG. 6B
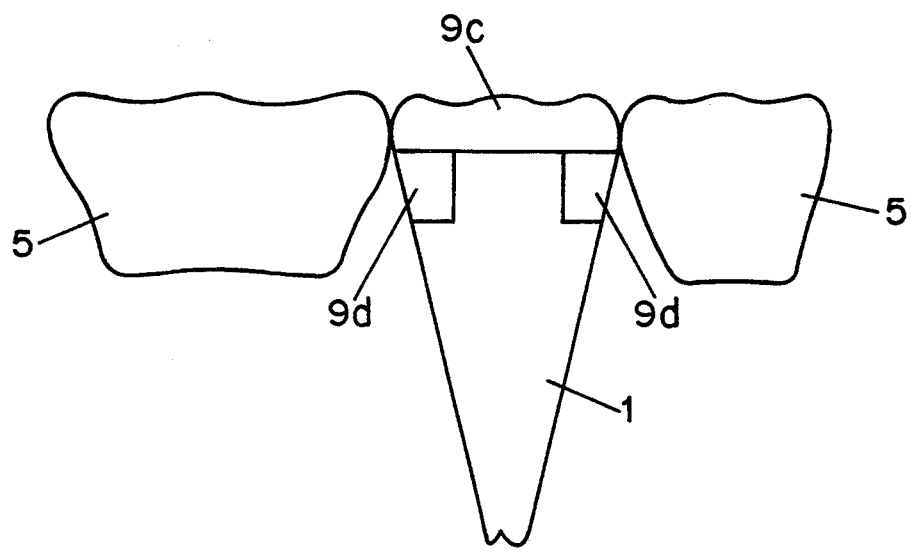
FIG. 7

METHOD FOR ADAPTING AND IMPLANTING A DENTAL PORCELAIN CHIP, AND THE CHIP

BACKGROUND OF THE INVENTION

The present invention relates to a method for adapting and implanting at least one dental porcelain chip in a cavity, in which the cavity and each porcelain chip is subjected to necessary etching, silanisation, and application of a binder before implantation takes place.

Characteristically, existing methods for placing fillings which are inexpensive to the patients are also technically/medically unsatisfactory, whereas methods providing qualitatively satisfactory results are very expensive. Now, a new method is proposed which provides optimal results to the patients at relatively reasonable costs.

Today there are two kinds of "filler materials". One kind consists of the plastic materials (amalgam, composites, and glassionomeric cement), which have the property of curing in the mouth. This group of fillers is inexpensive, but each material is separately connected with essential disadvantages. The other main group is prepared outside the mouth, before cementation in the mouth occurs. The point of this new method is to combine use of the main groups in such a manner that the advantages of both groups are achieved, at the same time as disadvantages are minimized.

In order to describe the present situation it should be mentioned that amalgam is a strong and inexpensive material, but it is aesthetically unsatisfactory and contains large amounts of mercury. It is, thus, on its way out now.

Composites (plastic fillers) are unsuitable in the molar area, and are not particularly suitable in the premolar areas (i.e. teeth behind the canine teeth). The load in these areas will readily cause fillings to crack and be prone to scaling. During the curing process the material, furthermore, is deformed with a consequent hazard of due to cracking injuries of the teeth as well as damage to the nerves.

Glassionomeric fillings are not very durable in areas with high loads.

Gold inlays are qualitatively first class, but often aestethically unsatisfactory, and they are also labour intensive and very expensive.

Composites may be manufactured by a dental technician in stead of being provided to form fillings. Most of the above mentioned disadvantages of composites may, in that case, be avoided, but the inlays still readily crack. Manufacture by a dental technician is also considerably more expensive.

Porcelain inlays or inserts which are manufactured by a dental technician may readily show porosities and may thus break. The laboratories of dental technicians do not permit manufacture of porcelain under optimal conditions of pressure and temperature. Also, porcelain inlays manufactured by technichians are very expensive.

Prefabricated or industrially produced porcelain is considerably stronger than the porcelain inlays, which may be manufactured in the technichian's laboratories. A recently developed system, the so called CAD-CAM, is based on fitting prefabricated porcelain blocks. The (only) CAD-CAM system on the market is introduced by Siemens and designated Cerec. This system is characterized by the fact that the porcelain inlay is grind fitted by the dentist by the aid of a machine. The system has the essential advantage that the inlay can be completed in one operation, and that it is unnecessary to involve a technichian. The result is a very robust porcelain filling. A disadvantage of the system is that it is initially very cost intensive. At present the system requires an investment of approximately NOK 300 000. Additionally, there are costs of material in the order of NOK 100 for each insert. Also, use of the system is quite complicated. Before the dentist manufactures an inlay, the preparation (excavation) must be photographed three-dimensionally by the aid of a special video camera. Photography requires optimal conditions and it may be difficult to achieve a useful result. It is necessary to screen the area by rubber dam (a special plastic mask), and to spray the tooth with a special powder to permit the camera to record shapes and differences of height. After photography an image of the tooth is displayed on a display unit. The dentist then draws the inlay proper on the display unit. Such drawing may seem complicated to many dentists.

As mentioned above, fitting of the inlay is carried out by the aid of a machine, which shows considerable technical limitations and thus, cannot fit all kinds of inlays. Before the inlay is cemented, it must be adapted to the tooth. It may be necessary to fit inside the inlay to get the inlay in place. Also, it must be adapted to the adjacent teeth. It is impossible to photograph the tooth and adjacent teeth in such a manner that one may draw the correct approximal relations (relation/points of contact with adjacent teeth) directly. In some cases it may also be very difficult to place the camera correctly, because clamps keeping the rubber dam in place may constitute an obstruction. This is in particular the case with the rearmost teeth. As regards the latter, it will always be difficult to provide a satisfactory inlay. For completeness it should be mentioned that it is not possible to achieve an optimal adaptation to the tooth. Between the inlay and tooth a crack is formed, which has to be filled with cement (composite). This, however, does not represent any significant disadvantage.

The CAD-CAM (Cerec-system) represents an substantial new development in the dental technical art. As will appear from the description above, the system is, however, relatively expensive in use. Also, it is complicated, labour intensive, and it has limitations as to applicability.

Before the new method is disclosed, cementation of Cerec-inlays should be described in more detail, because it shows points of resemblance with the proposed method.

When the Cerec-machine has completed preparation of the inlay, approximal relations must at first be adapted (i.e. adapted to adjacent teeth).

Then the porcelain inlay must be treated in a special manner to be able to bond to the composite. Etching with hydrofluoric acid is carried out to roughen the surface. Silanisation follows and a "bonding" or binder is put on and cured. This "bonding" bonds to the composite. Before photography, glassionomic cement is placed in the pulpal portion (bottom of the tooth) to protect the tooth and to prevent the nerve from dying. Cement is also used to align uneveness. Then, the enamel of the tooth is etched with phosphoric acid to be roughened. Then, a thin layer of "bonding" is blown into all uneven portions. The inlay may then be cemented by the aid of composite. At present, this is used by most dentists to cure composite. Finally, the inlay is fitted to the desired level and is polished.

SUMMARY OF THE INVENTION

We now propose utilizing a quite new manner of using mouldings in connection with adaption of prefabricated porcelain blocks, and preferably, in the shape of smaller porcelain chips. Traditionally, mouldings are only used to reproduce the patient's teeth to permit a dental technician to prepare the model. Now, it is suggested to utilize the moulding in a more direct or active manner.

This is achieved with a method of the kind described in the introduction above, which is characterized by the fact that a moulding is made of the cavity, that the moulding is fastened to the porcelain chip, that the porcelain chip is contoured to substantially the same shape as the moulding, and that the formed chip is disposed into the cavity and is fastened to the original tooth by means of a binder.

Since the cavity may be such that the tooth lacks one or more "side walls" (mesial, distal, buccal, lingual), the cavity may be sub-divided into one or a plurality of cavities (mesial, distal, buccal, lingual). The above paragraph should, thus also be understood to comprise a porcelain chip, the bottom surface of which is formed in addition to the side faces—i.e. either to be substantially plane or to comprise one or a plurality of "boxes", which correspond to the respective cavities and are integral with the remaining chip.

Advantageously, the porcelain chip may be fastened to the bottom of the moulding, preferably by glueing. The moulding may be removed again, before the chip is placed in the tooth cavity or after the chip is implated and fastened to the tooth.

In order to achieve the best results, the bottom surface and side faces of the tooth cavity are treated to extend at a mutual angle of substantially 90°.

Depending on the original form of the porcelain chip, the implanted porcelain chip may, upon curing of the binder be finely or height adapted to the tooth surface and the bite. This will commonly be carried out by grinding and polishing.

If the cavity comprises one or a plurality of sub-cavities, the moulding will have at least one "block" or "box" which may be removed before attachment of a porcelain chip for providing an occlusal inlay. The sub-cavities are then filled up with binder, filling material, or a separately formed porcelain chip.

For the moulding operation, a resilient material is used, which must be stable of shape and able to be accurately molded and must be curable in the mouth.

BRIEF DESCRIPTION OF THE DRAWINGS

Other and further objects, features, and advantages will appear from the following disclosure of a presently preferred embodiment of the invention, which is presented for illustration, without being limiting, and with reference to the appended drawings, in which FIG. 1A shows a tooth with an excavated cavity, and a distal, and mesial cavity, as seen from above;

FIG. 1B shows a mesio-distal section through the tooth/cavity of FIG. 1A;

FIG. 2A shows a moulding with a distal and mesial box in a perspective view;

FIG. 2B shows a cut moulding, which is glued onto a porcelain chip, as seen in perspective with the distal and mesial box cut away;

FIG. 2C shows a moulding and a ground porcelain chip which are still glued together;

FIG. 2D shows the cut moulding, as seen from above and glued onto the porcelain chip (the boxes are cut away);

FIG. 2E is an elevational view of the moulding before boxes are cut away;

FIG. 3A shows a top view of a cut off box glued onto a porcelain chip;

FIG. 3B shows the same as FIG. 3A in a distal view;

FIG. 3C shows the same as FIG. 3A in a buccal view;

FIG. 4A shows the cut off moulding being glued onto a porcelain chip, in a side elevation;

FIG. 4B is a distal view of FIG. 4A;

FIG. 5A shows an occluded cavity in a molar, as seen from above;

FIG. 5B shows a mesio-distal section through a molar, as shown in FIG. 5A,

FIG. 6A shows a top view of a cut moulding which is glued onto a porcelain chip, FIG. 6B shows a buccal elevation of the FIG. 6A, and FIG. 7 shows a tooth with a distal and a mesial chip, an occlusal chip, and adjacent teeth.

To follow is a more detailed description of the Figures, followed by a detailed discussion of necessary preparation and treatment of the cavity, the moulding, the inlay, and the filling. FIG. 1A shows a tooth 1, as seen from above. Occlusal excavating was carried out to form a central cavity 2, a distal (rear) cavity 3, and a mesial (front) cavity 4. FIG. 1B shows a mesio-distal section through tooth 1, as shown in FIG. 1A, along a longitudinal axis 8. The central, distal, and mesial cavities 2, 3 and 4, respectively, are indicated in the Figure. This Figure is only intended to be an example, since buccal and lingual cavities or excavations are treated in the same manner. When FIGS. 3 and 4 are discussed below, such excavations are, thus, meant as well.

FIG. 2A shows a moulding 10 with a top portion 10a and two approximal boxes 11, or a mesial and a distal box, which are finely cut off.

FIG. 2B shows the cut moulding 10a, which is glued to a porcelain chip 9.

FIG. 2C shows porcelain chip 9C after being cut to fit the shape of moulding 10a.

FIG. 2D shows the cut moulding 10a firmly glued to porcelain chip 9 in a diagrammatical top view. With a cavity as shown in FIGS. 1A and 1B, moulding 10 will just have the shape corresponding to the shape shown in FIG. 2A. As mentioned, these approximal boxes 11 may, if desired, be cut off. The cut-off approximal boxes 11 may, if desired, be glued onto a separate porcelain chip 9a, as shown in FIGS. 3A, 3B, and 3C. The completed chip is indicated by numeral 9d in FIG. 7.

Top portion 10a is shown in FIG. 4 to be glued to a porcelain chip 9, In an elevational (buccal) view. FIG. 4B shows the same as does FIG. 4A, but in an approximal view.

FIG. 5A shows another tooth 1' (molar) in a top view. This tooth 1' has a completely surrounded cavity 2' and has, thus, no open sides. FIG. 5B is a sectional view through tooth 1' according to FIG. 5A along centre line 8'.

FIG. 6A shows the associated, cut moulding 10b, which is glued onto a porcelain chip 9b, as seen in a top view. FIG. 6B shows a buccal elevation of the object of FIG. 6A with moulding 10b glued onto porcelain chip 9b.

FIG. 7 shows a tooth 1 placed between two adjacent teeth 5. Tooth 1 is prepared by the aid of two approximal chips 9i a, and an occlusal chip 9c.

DETAILED DESCRIPTION OF A PREFERRED EMBODIMENT

An implantation procedure is disclosed in more detail below and with further reference to the Figures.

A moulding 10 is made of cavity 2, 3, 4 (i.e. the excavated portion of the tooth) from a moulding material, e.g. a rubbery resilient material, in such a manner that the moulding material receives the same shape as the completed filling. This is a simple and rapid process. When the moulding material is cured, it is picked out by a probe. For further treatment of the inlay/filling, the shape of the cavity, in particular whether there is one or a plurality of faces, will be decisive. An occlusal inlay (FIGS. 5A–6B) (a filling on top of the tooth, i.e. one face) is easiest adapted. In order to achieve a good fit a quite plane bottom surface should be made in the cavity, as well as preferably vertical walls (i.e. 90° on the bottom surface). This is readily done by the aid of glassionomic cement. Upon making a moulding the latter is cut by the aid of a scalpel to provide the occlusal (uppermost) portion of the moulding with a face that is parallel with its bottom. The bottom of the moulding is glued to the most suitable porcelain chip in terms of longitudinal and transversal extension, thickness, and shape on the whole, and in view of a minimum of subsequent grinding work. The porcelain chip is then grinded in to shape it, apart from thickness, to correspond with the moulding as much as possible. Regarding the thickness of the porcelain chip, it should, from practical reasons, be slightly larger than the cut moulding. In this manner, the porcelain may be cemented before the moulding and porcelain are separated (cement is cured by light), which will simplify handling. Upon cementation the porcelain is grinded down to a correct level and is polished.

When two or more surfaces are involved (FIGS. 1A–4B), operations are based on the same principles. In order to achieve a good fit, it is advantageous for angles to be orthogonal in the internal portion of the cavity. In order to achieve this without removing more tooth substance than necessary, glassionomic cement may again be used in the inner portion of the cavity. Upon curing, the cement is grinded. Then, a matrix tape which should not be too high, is placed about the tooth and a moulding can be made.

When moulding 10 is cured and removed together with the matrix tape, the occlusal portion or cover 10a is cut by the aid of a scalpel to make the occlusal plane parallel with the pulpal floor of cavity 2, 3, 4. Since several faces are involved, there will now be one or a plurality of boxes 11 down on the sides (mesial, distal, buccal, lingual). Said boxes 11 may be cut off from moulding 10 and glued onto separate, suitable porcelain chips 9a, which are grinded in. When boxes 11 are removed, the bottom of remaining moulding 10a will be totally plane. The bottom is glued to a porcelain chip 9 and the porcelain chip is contour grinded to correspond to the moulding. This porcelain chip 9c will form the cover proper of the cavity. Porcelain chips 9a to be cemented in the distal and mesial cavities 3, 4 are now separated from the moulding, etched by hydrofluoric acid, silanised and provided with binder or bonding. Apart from the fact that moulding 10a is not removed from occlusal porcelain cover 9c, the latter is subjected to the same treatment. Tooth 1/cavity 2, 3, 4 is treated in the same manner as with Cerec-inlays. Then porcelain chips 9c, 9d may be integrally cemented with composite.

Many people will be of the opinion that it is the porcelain cover 9c proper which is the important member of such a filling, since it is here the forces from the teeth of the opposite jaw will act. A very good result may, thus, be achieved by filling the distal and mesial cavities with glassionomic cement (the filling variant), optionally, with composite, so that a quite totally "horizontal" surface is achieved before mouldings are made and the porcelain chip is adapted. The porcelain chip can then be cemented by the aid of dual cement.

It should be mentioned in this connection that at present, in use of white fillings, it is very common to provide glassionomic cement approximally and composite in layers occlusally. New caries attacks most often occur in the gingival (lowermost) area. Glassionomic cement releases fluorine, which will in turn counteract caries attacks. The composite is a strong material and will, additionally, bond strongly to etched enamel.

If there is no enamel gingivally, glassionomic cement should always be placed in this region because the material will also achieve a binding to dentin, in contrast with the composite.

Since composite does not bind to dentin, cementation of Cerec-inlays is at present not recommended, unless enamel is present about the entire preparation. Crevices of $100\mu$ between inlay and tooth commonly occur. The composite will shrink 2–3%, and if bondings are not as strong as those achieved to porcelain and etched enamel, there will be cracks of $2–3\mu$. A crack of $0.5\mu$ is sufficient for bacteria to penetrate, resulting in caries attacks.

It is possible that it will be recommended, for Cerec-inlays as well, to provide glassionomic cement gingivally before the moulding proper is made. In relatively many cases there will not be enamel present about the entire preparation and this is, in fact a question of cost and durability.

As regards the "porcelain chip" system, it might in these cases be a good concept to cement the approximate chips using of glassionomic cement before the occlusal cover is cemented by means of composite.

Another factor of substantial interest is that many today are of the opinion today that there should be at least a crack of $200\mu$ in order to achieve good curing of the composite. When the composite is cured, giant molecules are formed by means of free radicals. If there is too small a crack said free radicals will rapidly be absorbed by the walls, so that small molecules will be formed, causing the composite to have a rubberlike concistency.

This is of interest if anyone should object that a very good fit is perhaps not achieved by use of porcelain chips.

Another method which will no doubt provide a very good result is adaptation of the porcelain cover at first. When it is adapted it may be cemented directly by the aid of a composite.

At first, a translucent plastic matrix is provided about the tooth and wedging is done by the aid of reflexive plastic wedges. Then the cavity is filled with composite. The porcelain cover is then urged into place. Excessive filling material is removed and the material is cured. In this manner three essential advantages will be achieved: In the first place the pressure from the porcelain cover will urge filling material out laterally, so that there will be less porosities. Secondly, the pressure will cause the filling material to achieve better contact, i.e. binding to the enamel effectively. Thirdly, one does not have to provide composite in layers, since the composite layer will become so thin that it will not injure the pulpa (nerve) during curing. Before cementation, the porcelain chips and the teeth are treated with hydrofluoric acid, silane and bonding, as in the case of the Cerec-system.

In spite of the fact that the prefabricated porcelain is very hard and durable, it may readily and rapidly be shaped by the aid of a turbine (the most rapid dental drill). Due to this fact the number of prefabricated blocks or chips does not need to be very large.

In practice, the porcelain used for the Cerec-inlays also proved to "take" colour very well from the tooth. Apparently, there is neither a need for a large range of colours of the blocks of chips. There already exists a large range of colours of composites/glassiomeric cements used for cementation of the chips.

I claim:

1. A method for adapting a dental porcelain chip for implanting in a cavity within an original tooth, comprising:
   (a) making a molding of the cavity;
   (b) fastening the porcelain chip to the molding; and
   (c) contouring the porcelain chip to the same shape as the molding.

2. A dental porcelain chip for implanting in a cavity within an original tooth, formed in accordance with the process of claim 1.

3. A method for adapting and implanting a dental porcelain chip in a cavity within an original tooth, comprising the steps of:
   (a) making a molding of the cavity;
   (b) fastening the porcelain chip to the molding;
   (c) contouring the porcelain chip to the same shape as the molding;
   (d) placing the contoured porcelain chip in the cavity; and
   (e) fastening the contoured porcelain chip to the original tooth with a binder.

4. The method according to claim 3 wherein the porcelain chip is fastened to the bottom of the molding.

5. The method according to claim 4 wherein the porcelain chip is fastened to the bottom of the molding by glue.

6. The method according to claim 3 wherein the molding is removed before the porcelain chip is placed in the cavity.

7. The method according to claim 3 wherein the molding is removed after the porcelain chip is implanted and fastened to the original tooth.

8. The method according to claim 3 wherein cavity bottom and side surfaces are shaped to be substantially perpendicular to one another.

9. The method according to claim 3 wherein the porcelain chip, after being implanted in the cavity and fastened to the original tooth with a binder, is adapted to a patient's bite and surface finished so as to form a natural tooth in combination with the original tooth.

10. The method according to claim 3 for use when the cavity comprises at least one sub-cavity, further comprising:
    preceding step (b), a step of removing a sub-cavity portion of the molding; and
    preceding step (d), a step of filling the sub-cavity with a binder, a filling material or a separately fitted porcelain chip, so that, in step (d), the porcelain chip is placed as an occlusal inlay.

11. The method according to claim 3 wherein the molding comprises a resilient, form stable and accurately shapeable material which is curable in a mouth.

* * * * *